US011438995B2

(12) United States Patent
Uchiyama

(10) Patent No.: US 11,438,995 B2
(45) Date of Patent: Sep. 6, 2022

(54) RADIATION IMAGING SYSTEM, RADIATION IMAGING APPARATUS, RADIATION IMAGING METHOD, AND COMPUTER-READABLE MEDIUM

(71) Applicant: CANON KABUSHIKI KAISHA, Tokyo (JP)

(72) Inventor: Akehiko Uchiyama, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 67 days.

(21) Appl. No.: 16/593,032

(22) Filed: Oct. 4, 2019

(65) Prior Publication Data

US 2020/0037426 A1 Jan. 30, 2020

Related U.S. Application Data

(63) Continuation of application No. PCT/JP2018/013101, filed on Mar. 29, 2018.

(30) Foreign Application Priority Data

Apr. 6, 2017 (JP) ............................ JP2017-076303

(51) Int. Cl.
*H05G 1/42* (2006.01)
*G01N 23/04* (2018.01)
(Continued)

(52) U.S. Cl.
CPC ............... *H05G 1/42* (2013.01); *A61B 6/542* (2013.01); *G01N 23/04* (2013.01); *G01T 1/17* (2013.01)

(58) Field of Classification Search
None
See application file for complete search history.

(56) References Cited

U.S. PATENT DOCUMENTS 9,097,643 B2 8/2015 Tsuchiya
9,610,053 B2 4/2017 Okuno et al.
(Continued)

FOREIGN PATENT DOCUMENTS

JP 2004-24682 A 1/2004
JP 2008-145101 A 6/2008
(Continued)

OTHER PUBLICATIONS

Machine Translation JP 2011/041866 (Year: 2011).*
(Continued)

*Primary Examiner* — David P Porta
*Assistant Examiner* — Fani Boosalis
(74) *Attorney, Agent, or Firm* — Venable LLP

(57) ABSTRACT

Provided is a radiation imaging system configured to synchronize radiation irradiation with operation of a radiation imaging apparatus. The radiation imaging system includes: an irradiation unit arranged to irradiate with radiation; a detection unit arranged to detect the radiation; a setting unit configured to set an irradiation time at which irradiation of the radiation is to be started; an irradiation control unit configured to control the irradiation unit so that radiation irradiation is executed at the irradiation time; and a detection control unit configured to control the detection unit so that the detection unit is ready to detect the radiation at the irradiation time.

28 Claims, 11 Drawing Sheets

(51) Int. Cl.
*G01T 1/17* (2006.01)
*A61B 6/00* (2006.01)

(56) References Cited

U.S. PATENT DOCUMENTS

| | | | | |
|---|---|---|---|---|
| 10,856,834 | B2 | 12/2020 | Uchiyama et al. | |
| 2006/0215807 | A1 | 9/2006 | Ohara | |
| 2013/0170617 | A1 | 7/2013 | Tsuchiya | |
| 2013/0279661 | A1* | 10/2013 | Tamura | A61B 6/542 378/98 |
| 2015/0164459 | A1* | 6/2015 | Ito | G01T 1/2018 378/97 |
| 2016/0073989 | A1 | 3/2016 | Okuno et al. | |
| 2016/0157810 | A1 | 6/2016 | Tezuka | |

FOREIGN PATENT DOCUMENTS

| | | | |
|---|---|---|---|
| JP | 2011-19800 | A | 2/2011 |
| JP | 2013-138360 | A | 7/2013 |
| JP | 5404587 | B2 | 2/2014 |
| WO | 2014/108929 | A1 | 7/2014 |

OTHER PUBLICATIONS

International Preliminary Report on Patentability dated Oct. 8, 2019, in corresponding PCT/JP2018/013101 (11 pages).
Extended European Search Report dated Oct. 26, 2020, in counterpart application EP 18781430.6 (7 pages).

* cited by examiner

RADIATION IMAGING SYSTEM, RADIATION IMAGING APPARATUS, RADIATION IMAGING METHOD, AND COMPUTER-READABLE MEDIUM

CROSS-REFERENCE TO RELATED APPLICATIONS

This application is a Continuation of International Patent Application No. PCT/JP2018/013101, filed Mar. 29, 2018, which claims the benefit of Japanese Patent Application No. 2017-076303, filed Apr. 6, 2017, both of which are hereby incorporated by reference herein in their entirety.

BACKGROUND OF THE INVENTION

Field of the Invention

The present invention relates to a radiation imaging system, a radiation imaging apparatus, a radiation imaging method, and a computer-readable medium.

Description of the Related Art

A radiation imaging apparatus and a radiation imaging system with which a clear radiographic image is obtained by irradiating a subject with radiation from a radiation generating apparatus, digitizing the intensity distribution of radiation that has been transmitted through the subject, and performing image processing on the digitized radiographic image have been on the market.

It is common for a radiation imaging apparatus of this system to use an image pickup element for an image receiver (radiation detector). The operation of a common image pickup element involves repeating the accumulation of electric charges in an amount dependent on incident light, the reading of the accumulated electric charges, and the resetting of the electric charges. An image pickup element without an electronic shutter has a risk of ruining an image when light enters the image pickup element during the reading or resetting of the electric charges.

In a system disclosed in Japanese Patent No. 5404587, a message signifying a photographing request and a message signifying the completion of photographing preparations are transmitted and received over a network line in order to synchronize operation timing of an image pickup element and radiation irradiation.

However, messages have a characteristic that the messages may be lost or delayed over a network line. The system disclosed in Japanese Patent No. 5404587 therefore executes the synchronization by allowing for a time margin in an image receivable period of a radiation imaging apparatus, in other words, lowering the accuracy of a required time for the synchronization.

The image receivable period of the radiation imaging apparatus may expire while messages for the synchronization are lost or delayed over a network line. There is consequently a problem that it is difficult to establish synchronization by transmitting and receiving the messages each time radiation irradiation is executed.

The present invention provides a radiation imaging system configured to synchronize radiation irradiation with the operation of a radiation imaging apparatus.

SUMMARY OF THE INVENTION

According to one exemplary embodiment of the present invention, there is provided a radiographic moving image photographing system including: an irradiation unit arranged to irradiate with radiation; a detection unit arranged to detect the radiation; a setting unit configured to set an irradiation time at which irradiation of the radiation is to be started; an irradiation control unit configured to control the irradiation unit so that radiation irradiation is executed at the irradiation time; and a detection control unit configured to control the detection unit so that the detection unit is ready to detect the radiation at the irradiation time.

Further features of the present invention will become apparent from the following description of exemplary embodiments with reference to the attached drawings.

DESCRIPTION OF THE EMBODIMENTS

Embodiments of the present invention will now be described in detail with reference to the attached drawings.

However, details of dimensions and structures given in the embodiments are not limited to those in the description and the drawings. Radiation here includes, in addition to X-rays, α-rays, β-rays, γ-rays, various particle rays, and the like.

First Embodiment

Figure 1:
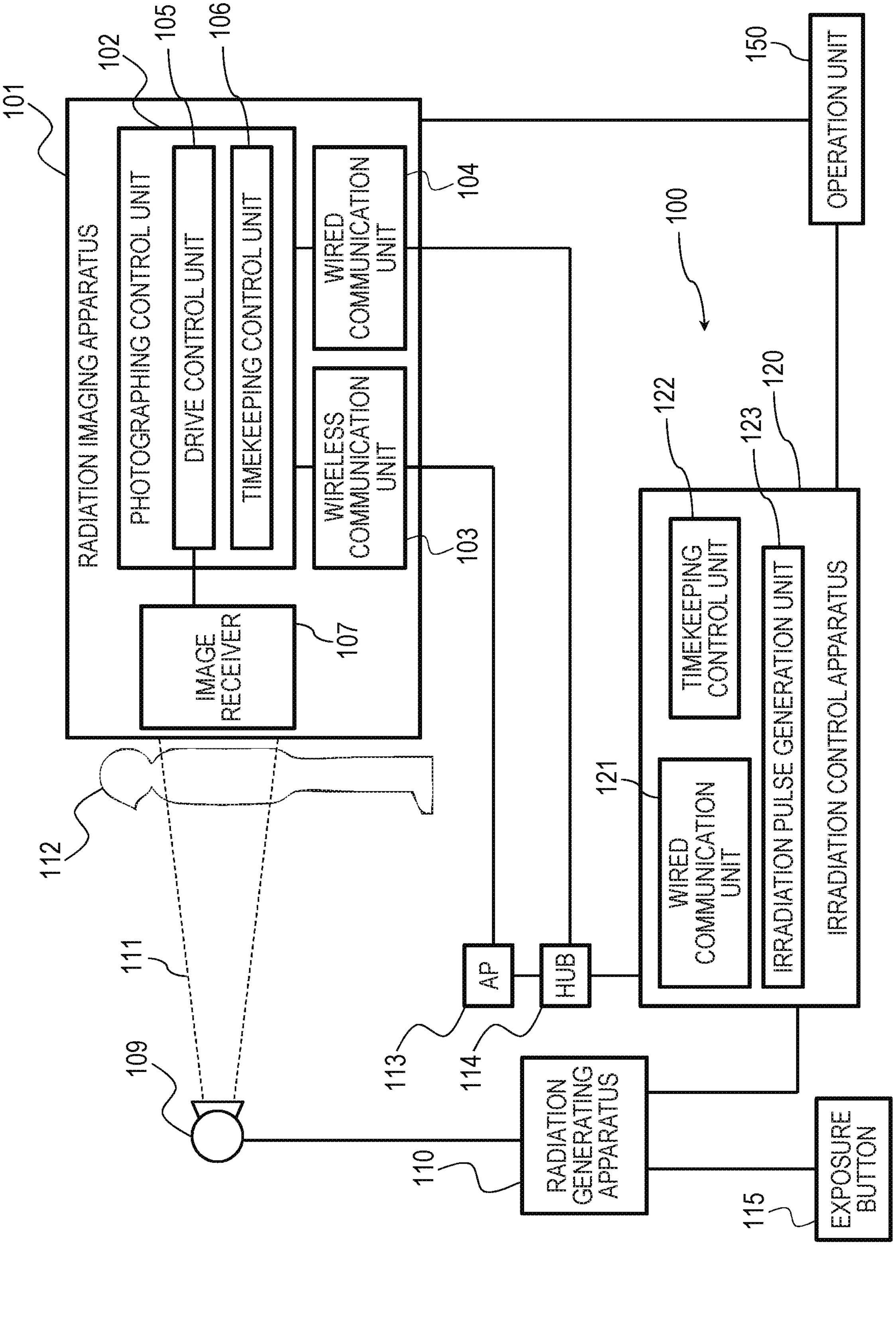
FIG. 1 is a diagram for illustrating a configuration example of a radiation imaging system according to a first embodiment of the present invention.

A radiation imaging system according to a first embodiment of the present invention is illustrated in FIG. 1. A radiation imaging system 100 includes a radiation imaging apparatus (detection control unit) 101, a radiation generating apparatus (irradiation unit) 110, and an irradiation control apparatus (irradiation control unit) 120 configured to control the radiation generating apparatus 110. The radiation imaging apparatus 101 includes a wired communication unit 104. The irradiation control apparatus 120 includes a wired communication unit 121. The communication units connect the radiation imaging apparatus 101 and the irradiation control apparatus 120 to each other via a communication network, which includes a HUB 114 and others.

The radiation imaging apparatus 101 may include a wireless communication unit 103. In this case, a wireless LAN access point (AP) 113 is included in the infrastructure of the communication network, and a section that is a part of the communication network is connected by wireless communication with the use of the wireless communication unit 103 and the wireless LAN access point (AP) 113. Information is exchanged in a message format between pieces of equipment that are connected to each other via the communication network.

Connection between the radiation generating apparatus 110 and the irradiation control apparatus 120, on the other hand, is direct electric connection, which involves no communication network. Information is accordingly transmitted directly between the radiation generating apparatus 110 and the irradiation control apparatus 120 as an electric signal, without being converted into a message format.

The radiation imaging apparatus 101 is an apparatus configured to obtain radiographic image data of a subject 112 based on radiation 111 that has been radiated from a radiation source 109 and transmitted through the subject 112. For example, a radiation imaging apparatus using a flat panel detector (FPD) is used suitably as the radiation imaging apparatus 101.

The radiation imaging apparatus 101 includes, at least, an image receiver (detection unit) 107 configured to generate radiographic image data based on received radiation, and a photographing control unit 102. The radiation imaging apparatus 101 controls the image receiver 107, which detects radiation. The photographing control unit 102 drives and controls the image receiver 107, performs various types of image processing on radiographic image data of a photographed radiographic image, stores the radiographic image data, determines the timing of transferring the radiographic image data, and performs processing related to the control of transfer of the radiographic image data. The radiographic image data processed by the photographing control unit 102 is transferred to a control terminal (not shown) to be provided for examination or other uses.

The radiation imaging system 100 is adapted to photograph a radiographic image in the form of a moving image, and operation thereof is outlined as follows. At first, prior to the photographing, parameters for photographing a moving image (e.g., the frame rate and the length of a radiation pulse per frame) are set in advance to relevant units of the system.

An operation unit 150 is a setting unit for setting an irradiation time at which radiation irradiation is executed. An operator is allowed to set any irradiation time via the operation unit 150. The irradiation time set in the operation unit 150 is transmitted to the irradiation control apparatus 120 and the radiation imaging apparatus 101. The operation unit 150 may have a function of displaying a radiographic image that is output from the radiation imaging apparatus 101. The irradiation time may also be set with an exposure button 115. The operator of the radiation imaging system presses the exposure button 115 at desired timing of photographing. The press of the exposure button 115 is transmitted as an electric signal to the irradiation control apparatus 120. The irradiation control apparatus 120 receives the signal, sets the irradiation time at which radiation irradiation is to be started, generates a message to the effect that photographing is started, and exchanges messages with the radiation imaging apparatus 101 over the communication network.

After the irradiation time is transmitted, an irradiation pulse generation unit 123 in the irradiation control apparatus 120 generates a timing pulse for radiation irradiation. A timekeeping control unit 122 in the irradiation control apparatus 120 holds time information. The irradiation pulse generation unit 123 generates the timing pulse based on the time information of the timekeeping control unit 122. The timing pulse is transmitted to the radiation generating apparatus 110, and the radiation generating apparatus 110 irradiates with the radiation 111 at timing indicated by the timing pulse.

Meanwhile, in the radiation imaging apparatus 101 after the transmission of the irradiation time, a drive control unit 105 in the photographing control unit 102 generates a drive control signal for the image receiver 107, and obtains radiographic image data from the image receiver 107. A timekeeping control unit 106 in the radiation imaging apparatus 101 holds time information. The drive control unit 105 generates the drive control signal based on the time information of the timekeeping control unit 106.

The radiographic image data is obtained at a time selected to avoid an overlap with the timing pulse for radiation irradiation. In short, the radiographic image data is obtained in a time slot different from a time slot for radiation irradiation.

When the operator of the radiation imaging system stops pressing the exposure button in order to end the photographing, the irradiation control apparatus 120 stops generating the timing pulse, generates a message to the effect that photographing is to be stopped, and exchanges messages with the radiation imaging apparatus 101.

The procedure of communicating messages with which the start of photographing and the stopping of photographing are controlled and the generation of operation timing, which are described above, are described in detail with reference to FIG. 2.

The radiation imaging apparatus 101 and the irradiation control apparatus 120 include the timekeeping control unit 106 and the timekeeping control unit 122, respectively, which perform timekeeping operation with the time of activation of the radiation imaging system as a starting point. The time on the radiation imaging apparatus 101 and the time on the irradiation control apparatus 120 are synchronized prior to photographing. The method of the synchronization is described later.

When an irradiation time at which radiation irradiation is to be executed is set by the operation unit 150, the irradiation control apparatus 120 obtains the current time from the timekeeping control unit 122. The irradiation control apparatus 120 obtains the current time from the timekeeping control unit 122 also when the exposure button is pressed. In FIG. 2, the irradiation control apparatus 120 obtains a time value 10260 from the timekeeping control unit 122.

The irradiation time at which radiation irradiation is to be started is transmitted to the irradiation control apparatus 120. Specifically, a scheduled exposure start time at which exposure is to be started is set to a time that succeeds the current time by a given amount of time. The scheduled exposure start time is calculated by adding a preset amount of time to the current time.

The amount of time to be added is large enough for the radiation imaging apparatus 101 and the irradiation control apparatus 120 to transmit (exchange messages), and large enough for the radiation imaging apparatus 101 to shift to photographing preparation operation, which involves radiation detection. The amount of time to be added may also be set small enough to avoid giving the operator an impression of poor operability from unnecessary waiting. The value of the amount of time to be added may be calculated and set in advance, at the time of designing the system, or may be determined dynamically by advance negotiation through communication between the irradiation control apparatus 120 and the radiation imaging apparatus 101.

The value of the amount of time to be added is not described in detail here. In the example of FIG. 2, however, a time value 40 is added to calculate a scheduled exposure start time 10300.

After the scheduled exposure start time is calculated, the irradiation control apparatus 120 transmits irradiation information about the irradiation time at which radiation irradiation is to be started (the scheduled exposure start time) to the radiation imaging apparatus 101. The irradiation control apparatus 120 transmits, to the radiation imaging apparatus 101, a photographing request message 200 requesting the radiation imaging apparatus 101 to start photographing. The photographing request message 200 includes, as a parameter, the scheduled exposure start time described above.

Figure 2:
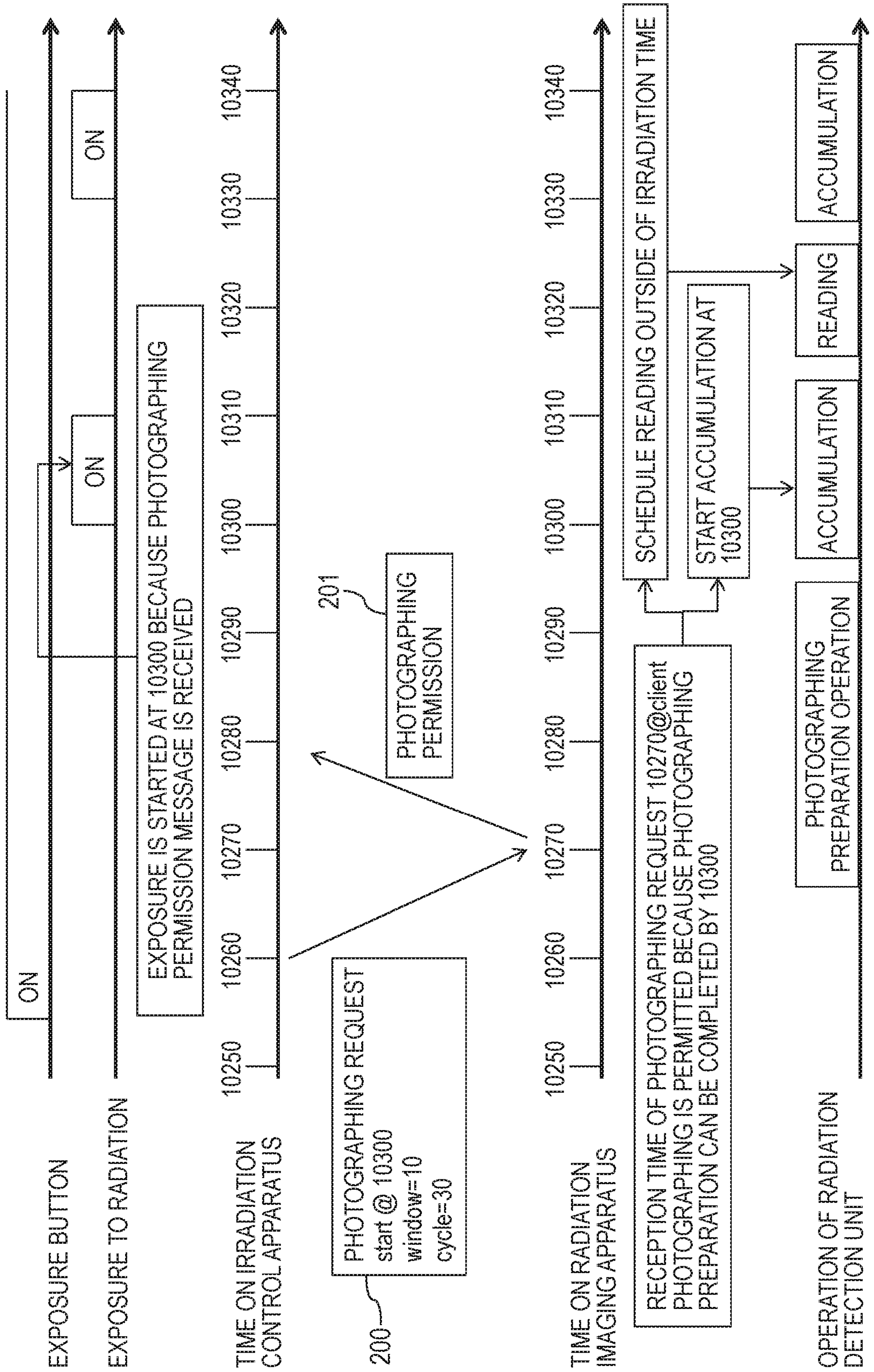
FIG. 2 is a diagram for illustrating an example of a procedure of communicating messages with which the start of photographing and the stopping of photographing are controlled.

In FIG. 2, the photographing request message 200 includes information equivalent to the length of radiation irradiation time (the length of a radiation pulse, an irradiation window, or the like) and information equivalent to the irradiation cycle (the frame rate or the like). These pieces of information, however, are not required to be included in the photographing request message 200, and may be set or transmitted by other measures prior to photographing as described above. Other parameters that are not explicitly described here may be included in the photographing request message 200 to be transmitted.

The irradiation time at which radiation irradiation is to be started is transmitted to the radiation imaging apparatus 101 from the outside. For example, the radiation imaging apparatus 101 receives the photographing request message 200 and, at the time the photographing request message 200 is received, obtains the current time from its own timekeeping control unit 106. The radiation imaging apparatus 101 compares the current time to the scheduled exposure start time received in the message, and determines whether the photographing preparation operation (or radiation detection operation) can be completed by the scheduled exposure start time in light of a photographing mode that is to be used in the upcoming photographing.

When it is determined as a result that the photographing preparation operation can be completed, the radiation imaging apparatus 101 transmits a photographing permission message 201 permitting photographing (or radiation irradiation) to the irradiation control apparatus 120 in response, and schedules the photographing preparation operation. The photographing preparation operation is executed by the driving control unit 105.

In this manner, the photographing control unit 102 receives the irradiation information about the irradiation time at which radiation irradiation is to be started, and the radiation imaging apparatus 101 performs control that causes the image receiver 107 to be ready for radiation detection at the irradiation time, based on the irradiation information (the scheduled exposure start time). The radiation imaging apparatus 101 also transmits photographing permission information (the photographing permission message 201), which indicates that the image receiver 107 is expected to be ready to detect radiation at the irradiation time and can photograph the radiation, to the irradiation control apparatus 120.

When the photographing permission message 201 is received by a point in time that precedes the irradiation time (that precedes the scheduled exposure start time) by a given amount, the irradiation control apparatus 120 controls the radiation generating apparatus 110 to execute radiation irradiation. For example, when the photographing permission message 201 is received before the time indicated by its own timekeeping control unit 122 reaches the scheduled exposure start time, the irradiation control apparatus 120 starts generating the timing pulse for radiation irradiation at the scheduled exposure start time. The irradiation control apparatus 120 then schedules, based on the time that is measured by the timekeeping control unit 122, radiation irradiation operation so that a radiation pulse length and a frame rate that are determined in advance are reached, and the irradiation pulse generation unit 123 executes the radiation irradiation operation.

The irradiation control apparatus 120 thus controls the radiation generating apparatus (irradiation unit) 110 to irradiate with radiation at the irradiation time.

The radiation imaging apparatus 101 meanwhile completes the photographing preparation operation and, when the time indicated by its own timekeeping control unit 106 reaches the scheduled exposure start time, shifts the operation of the image receiver 107 to an accumulation state in anticipation for radiation irradiation. After an amount of time equivalent to the length of a radiation pulse elapses (in FIG. 2, after the time indicated by the timekeeping control unit 106 reaches 10310), the image receiver 107 shifts from the accumulation state to a reading state, in which accumulated electric charges (information) are read, and radiographic image data is obtained based on the read electric charges.

The radiation imaging apparatus 101 then schedules, as in the irradiation control apparatus 120, based on the time that is measured by the timekeeping control unit 106, photographing operation (accumulation operation, reading operation, and the like) so that a frame rate determined in advance is reached, and the photographing operation is executed by the photographing control unit 102.

Figure 3:
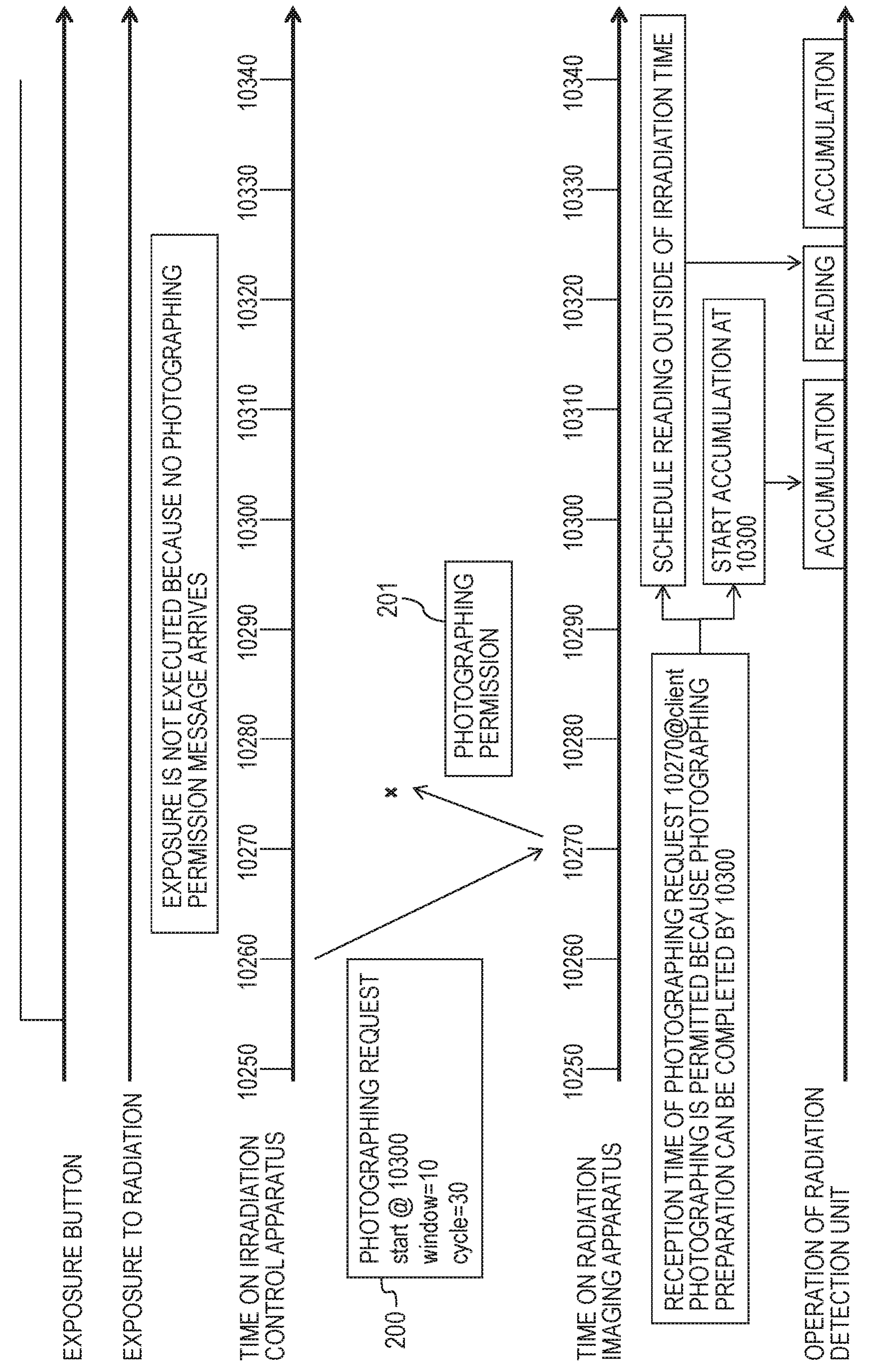
FIG. 3 is a diagram for illustrating an example in which a message for starting photographing has not arrived.

As described above, the irradiation control apparatus 120 generates the timing pulse for radiation irradiation on the condition that the photographing permission message 201 is received. Operation executed when this condition is not fulfilled due to the loss or large delay of a message over the communication network is illustrated in FIG. 3.

In the event of a failure to receive the photographing permission message 201, the irradiation control apparatus 120 generates no pulse even when the time indicated by the timekeeping control unit 106 reaches the scheduled exposure start time 10300. Meanwhile, the radiation imaging apparatus 101, which has no way of finding out whether the photographing permission message 201 transmitted by the radiation imaging apparatus 101 has reached the irradiation control apparatus 120, starts obtaining radiographic image data at the scheduled exposure start time 10300. The radiation imaging apparatus 101 consequently receives a dark image, which is generated without irradiation. This is photographing operation in which the subject is not irradiated with radiation, and accordingly causes no harm from unnecessary exposure.

The irradiation control apparatus 120 thus performs control that prevents the radiation generating apparatus 110 from executing radiation irradiation, when the photographing permission information is not received by a point in time that precedes the irradiation time (that precedes the scheduled exposure start time) by a given amount.

The loss of the photographing permission message 201 described above is not the only cause of the phenomenon in which the photographing permission message 201 fails to arrive. Other causes include the loss of the photographing request message 200, which leads to no transmission of the photographing permission message 201 from the radiation imaging apparatus 101 to begin with, and a delay of the photographing request message 200. There is also a case in which the radiation imaging apparatus 101 determines that photographing is inexecutable for reasons pertaining to the radiation imaging apparatus 101, and accordingly does not transmit the photographing permission message 201 in response.

When photographing is inexecutable, the radiation imaging apparatus 101 may transmit a photographing prohibition message (abnormality message) to the irradiation control apparatus 120 in response in place of the photographing permission message 201. In any case, unnecessary irradiation of the subject with radiation is avoided.

Photographing continuation determination and stopping of photographing are described next. There are a plurality of situations in which radiation irradiation is to be stopped. An example of the situations is a case in which the operator of the radiation imaging system stops pressing the exposure button 115, to thereby stop photographing. This is normal stop. An example of abnormal stop is a case in which the irradiation control apparatus 120 detects abnormality in the photographing operation of the radiation imaging apparatus 101 or the like.

After exchanging a message that indicates the start of photographing, the radiation imaging apparatus 101 keeps periodically transmitting a normality message 202 to the irradiation control apparatus 120 for the duration of the photographing operation. The irradiation control apparatus 120 determines that the radiation imaging apparatus 101 is operating normally as long as the normality message 202 is kept received.

The radiation imaging apparatus 101 thus transmits normality information (the normality message), which indicates that the image receiver 107 is operating normally, to the irradiation control apparatus 120 when the image receiver 107 is allowed to detect radiation. The irradiation control apparatus 120 determines whether the image receiver 107 is normal or abnormal based on the normality information. The irradiation control apparatus 120 performs control that causes the radiation generating unit 110 to execute radiation irradiation when the image receiver 107 is normal, and performs control that prevents the radiation generating apparatus 110 from executing radiation irradiation when the image receiver 107 is abnormal.

In short, the irradiation control apparatus 120 controls the radiation generating unit 110 so that radiation irradiation is executed based on the normality information.

The normality message 202 itself may be lost over the communication network. It may accordingly be excessive for the irradiation control apparatus 120 to determine that the radiation imaging apparatus 101 has abnormality just from one occurrence of missing of the normality message 202. The irradiation control apparatus 120 may therefore determine whether the radiation imaging apparatus 101 has abnormality from the frequency of the missing of the normality message 202. The interval between the transmission and reception of the normality message 202 may be set to a time interval less than a given threshold value for the purpose of quick determination. The threshold value, however, may be set to a long time interval that is not a burden on the communication network.

As described above, the irradiation control apparatus 120 performs control so that the radiation generating apparatus 110 irradiates with the radiation, based on at least one of reception/non-reception of the normality message, a frequency of the reception, an interval of the reception, a time of the reception, and the number of received normality messages.

Figure 5:
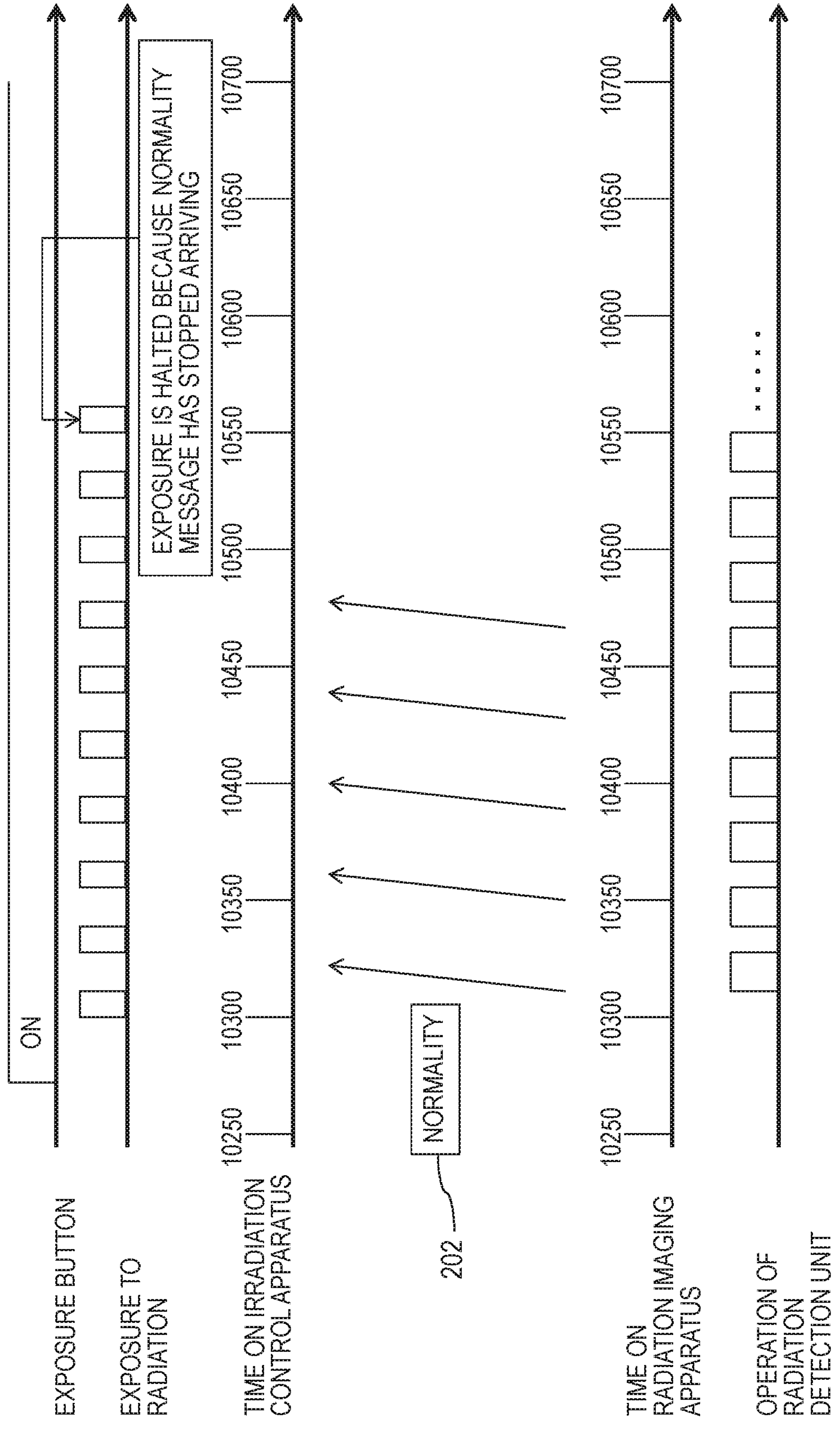
FIG. 5 is a diagram for illustrating an example of the transmission of a normality message and the stopping of photography due to missing of the normality message.

What happens when there is missing of a normality message 202 is illustrated in FIG. 5. When the missing of the normality message 202 arriving at the irradiation control apparatus 120 occurs at an unacceptable frequency (equal to or higher than a given threshold value), the irradiation control apparatus 120 stops generating the timing pulse for radiation irradiation to stop exposure. The irradiation control apparatus 120 stops exposure without determining the state of the radiation imaging apparatus 101 or the communication network that has caused the non-arrival of the normality message 202, such as abnormality in the photographing operation of the radiation imaging apparatus 101 or a trouble in the communication network.

Exposure may accordingly be stopped while the radiation imaging apparatus 101 continues the photographing operation. The radiation imaging apparatus 101 in this case obtains a dark image, which is generated without irradiation. This is photographing operation in which the subject is not irradiated with radiation, and accordingly causes no harm from unnecessary exposure.

The description given above is about the stopping of exposure due to a failure of the irradiation control apparatus 120 to passively determine whether the operation of the radiation imaging apparatus 101 is normal or abnormal based on the normality message 202. The photographing operation or the exposure operation is stopped also when the radiation imaging apparatus 101 actively notifies its own abnormality to the irradiation control apparatus 120.

Figure 6:
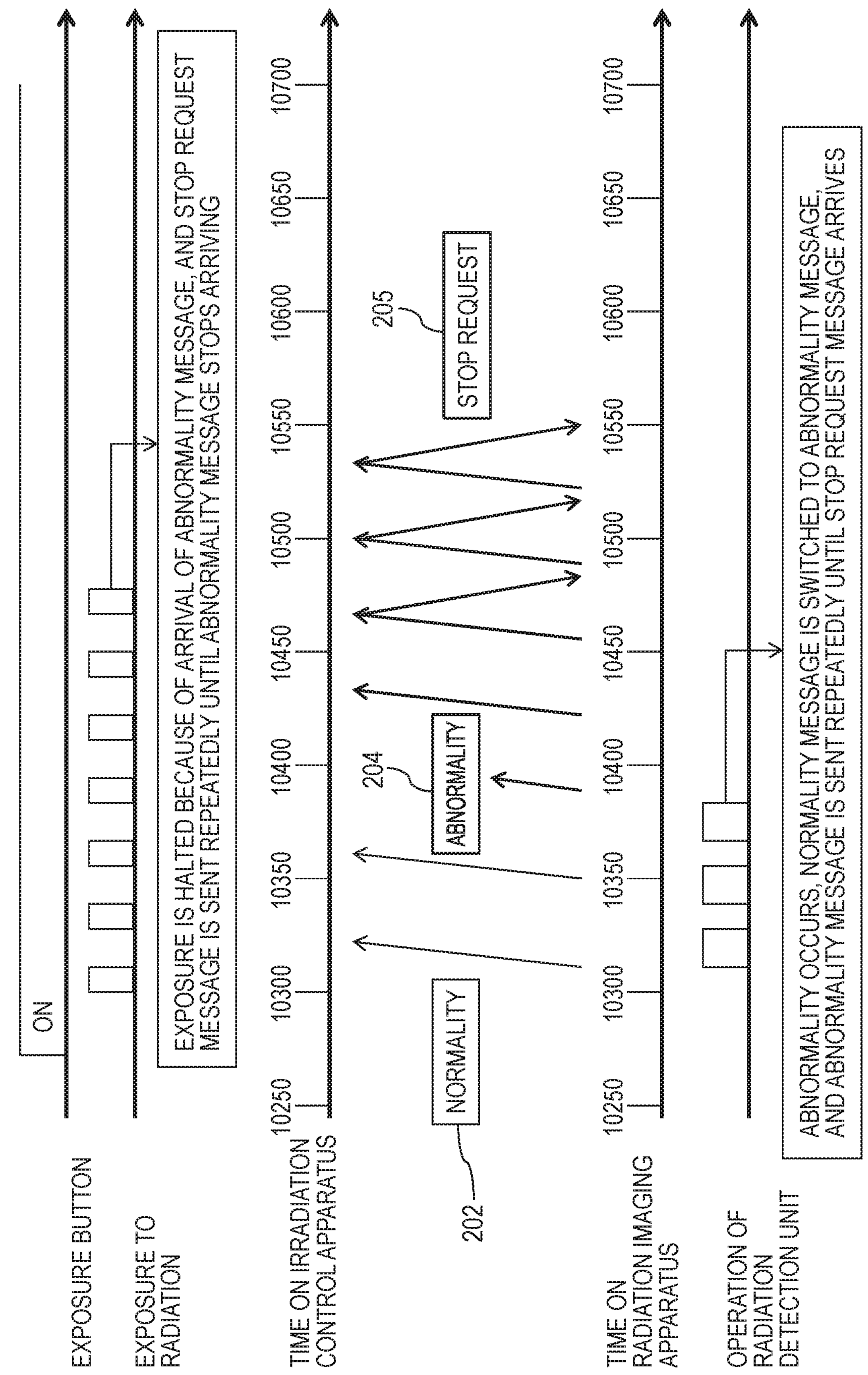
FIG. 6 is a diagram for illustrating an example of stopping photographing due to an abnormality message.

The notification is illustrated in FIG. 6. When detecting abnormality in its own operation and determining that image receiving operation cannot be maintained, the radiation imaging apparatus 101 stops transmitting the normality message 202 and starts transmitting the abnormality message 204. The transmission of the abnormality message 204 is repeated periodically as is the case for the normality message 202. When the abnormality message 204 arrives at the irradiation control apparatus 120, the irradiation control apparatus 120 immediately stops generating the timing pulse for radiation irradiation, without waiting for the determination of the frequency of the missing of the normality message 202. The irradiation control apparatus 120 then transmits a stop request message 205 to the radiation imaging apparatus 101 in response.

The radiation imaging apparatus 101 thus transmits abnormality information (the abnormality message), which indicates that the image receiver 107 is not operating normally, to the irradiation control apparatus 120 when the image receiver 107 is unavailable to detect radiation (also when the image receiver 107 is unavailable to output the predetermined radiographic image data). The irradiation control apparatus 120 determines whether the image receiver 107 is normal or abnormal based on the abnormality information. The irradiation control apparatus 120 performs control that causes the radiation generating apparatus 110 to execute radiation irradiation when the image receiver 107 is normal, and performs control that prevents the radiation generating apparatus 110 from executing radiation irradiation when the image receiver 107 is abnormal.

When the abnormality information is received, the irradiation control apparatus 120 determines that there is abnormality in the image receiver 107, and performs control that prevents the radiation generating apparatus 110 from executing radiation irradiation. When the radiation generating apparatus 110 stops radiation irradiation, the irradiation control apparatus 120 transmits, to the radiation imaging apparatus 101, stop request information (stop request message) requesting the image receiver 107 to stop operating.

Each time the abnormality message 204 arrives, the irradiation control apparatus 120 transmits the stop request message 205 in response. The radiation imaging apparatus 101 stops the repeated transmission of the abnormality message 204 when the stop request message 205 is received from the irradiation control apparatus 120. This completes the procedure of abnormal stop. The transmission interval of the abnormality message 204 is not required to be the same as the transmission interval of the normality message 202. The transmission interval of the abnormality message 204 can be set as short as possible in order to quickly inform of abnormality, and may be shorter than the transmission interval of the normality message 202.

Figure 4:
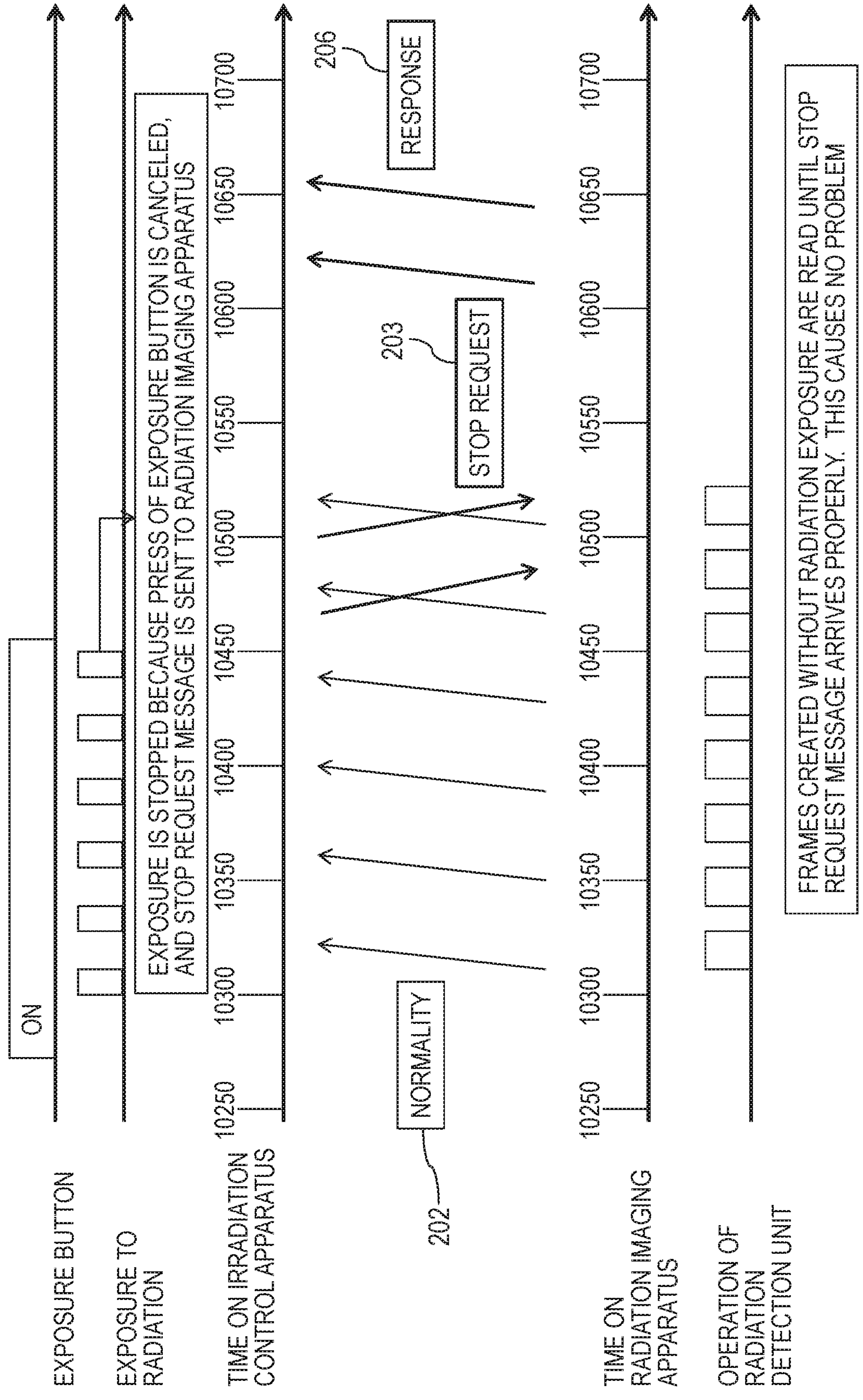
FIG. 4 is a diagram for illustrating an example of a communication procedure for stopping photographing.

Normal stop by an input from the operator is described next with reference to FIG. 4. When the operator stops pressing the exposure button 115, a stop signal is transmitted to the irradiation control apparatus 120. The irradiation control apparatus 120 receives the stop signal and immediately stops generating the timing pulse for radiation irradiation. The irradiation control apparatus 120 then transmits a stop request message 203 to the radiation imaging apparatus 101. The radiation imaging apparatus 101 receives the stop request message 203 and stops the photographing operation.

The radiation imaging apparatus 101 confirms the stop request message 203, and transmits a response message 206 to the irradiation control apparatus 120. The irradiation control apparatus 120 repeatedly transmits the stop request message 203 to the radiation imaging apparatus 101 until the response message 206 arrives at the irradiation control apparatus 120. To summarize, when receiving the stop request information, the radiation imaging apparatus 101 transmits response information (response message) indicating that the stop request information has been received to the irradiation control apparatus 120, and the irradiation control apparatus 120 stops transmitting the stop request information when the response information is received. This completes the normal stop.

The stop request message 203 may be lost over the communication network, and exposure may accordingly be stopped while the radiation imaging apparatus 101 continues the photographing operation. The radiation imaging apparatus 101 in this case obtains a dark image, which is generated without irradiation. This is photographing operation in which the subject is not irradiated with radiation, and accordingly causes no harm from unnecessary exposure.

Figure 7:
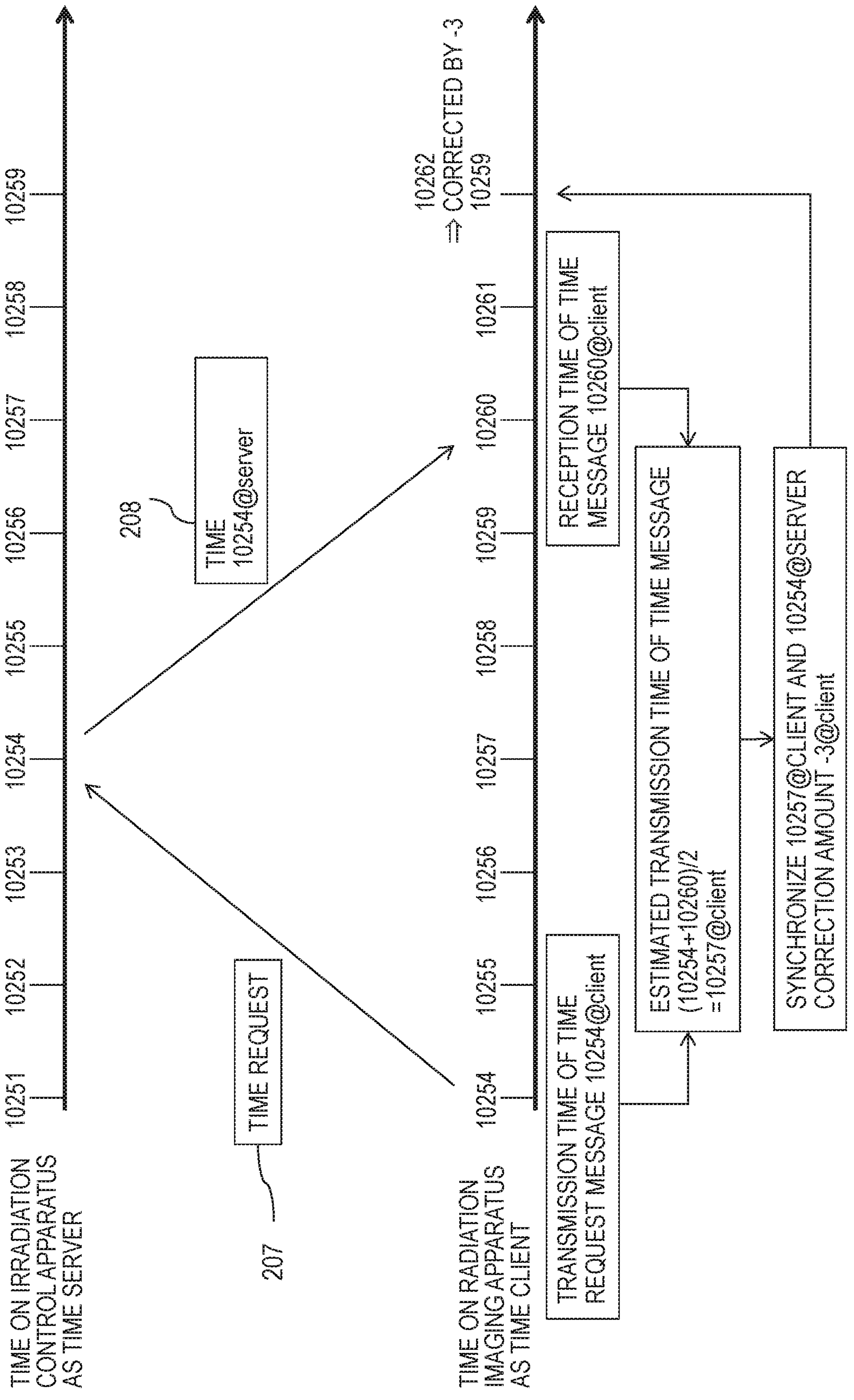
FIG. 7 is a diagram for illustrating an example of a communication procedure of time synchronization processing.

This concludes the description on the procedure of communicating messages with which the start of photographing and the stopping of photographing are controlled. The mechanism of, and a communication procedure for synchronizing the time that is measured by the timekeeping control unit 106 and the time that is measured by the timekeeping control unit 122 are described next. A procedure of establishing time synchronization through communication over the communication network is illustrated in FIG. 7. In FIG. 7, the timekeeping control unit 122 operates as a time server (i.e., a clock that serves as a reference), and the timekeeping control unit 106 operates as a time client (i.e., a clock that is corrected with the time server as a reference).

First, the radiation imaging apparatus 101 transmits, to the irradiation control apparatus 120, a time request message 207 requesting the irradiation control apparatus 120 to transmit the time (time information) of the timekeeping control unit 122, via the wired communication unit 104 or the wireless communication unit 103. The time request message 207 includes a transmission time at which the time request message 207 is transmitted in the radiation imaging apparatus 101 (the time measured by the timekeeping control unit 106). In the example of FIG. 7, a time value 10254 is included in the time request message 207.

The irradiation control apparatus 120 receives the time request message 207, and transmits a time message 208 to the radiation imaging apparatus 101 in response. The time message 208 includes a transmission time at which the time message 208 is transmitted in the irradiation control apparatus 120 (the time measured by the timekeeping control unit 122). In FIG. 7, a time value 10254 is included in the time message 208. When the time message 208 arrives at the radiation imaging apparatus 101, the radiation imaging apparatus 101 obtains the time of reception of the time message 208 in terms of time measured by the timekeeping control unit 106. In FIG. 7, a time value 10260 is obtained.

It is assumed that the time request message and the time message 208 are transmitted in substantially equal times between the radiation imaging apparatus 101 and the irradiation control apparatus 120. In this case, a time at which the irradiation control apparatus 120 transmits the time message 208 in response is estimated to be the middle between the time value 10254 and the time value 10260 ((10254+10260)/2=10257) in terms of time measured by the timekeeping control unit 106.

The time value 10254 of the irradiation control apparatus 120 is included in the time message 208, and it is accordingly found that the clock on the radiation imaging apparatus 101 is fast by a time difference between the time value 10254 and the estimated time, which is calculated as 10257−10254=3. With the time difference between the timekeeping control unit 106 and the timekeeping control unit 122 calculated in the manner described above, the time that is measured by the timekeeping control unit 106 and the time that is measured by the timekeeping control unit 122 can be synchronized by correcting the time that is measured by the timekeeping control unit 106.

The radiation imaging apparatus 101 thus corrects the time information that is referred to by the radiation imaging apparatus 101 (the time measured by the timekeeping control unit 106) based on the time information that is referred to by the irradiation control apparatus 120 (the time measured by the timekeeping control unit 122). In the first embodiment, the radiation imaging apparatus 101 corrects the time information that is referred to by the radiation imaging apparatus 101 based on the time information that is referred to by the irradiation control apparatus 120, a transmission time at which the time request information is transmitted, and a reception time at which the time information is received from the irradiation control apparatus 120 in response to the time request information.

The irradiation control apparatus 120 may store the time difference to control the radiation source 109 and the radiation imaging apparatus 101 based on the time that is measured by the timekeeping control unit 122 and that has been adjusted by the stored time difference. The radiation imaging apparatus 101 may store the time difference and add the time difference to the time that is measured by the timekeeping control unit 106 to operate at operation timing specified by the irradiation control apparatus 120.

In FIG. 7, a correction amount of the correction is determined based on the one transmission/reception session of the time request message 207 and the time message 208. In practice, however, the correction amount may require an adjustment because of possible fluctuations in message propagation time. A plurality of transmission/reception sessions of the time request message 207 and the time message 208 may therefore be executed to statistically calculate the correction amount.

For example, the correction amount may be calculated statistically by picking up a given number of correction amounts in ascending order of round-trip time from among correction amounts based on a plurality of transmission/reception sessions of the time request message 207 and the time message 208, and calculating an average of the given number of correction amounts. The round-trip time in the first embodiment is a period of time that starts with the transmission of the time request message 207 from the radiation imaging apparatus 101 and that ends with the reception of the time message 208 at the radiation imaging apparatus 101. The correction amount may also be calculated from a time difference in an acceptable error range, which is based on the period of radiation irradiation relative to the period of the accumulation state.

The correction amount is added at once in the description given above. However, a large correction made at once significantly impairs the equality of intervals in the drive control of the image receiver 107 immediately after the correction, and the impairment causes a phenomenon in which only one frame conspicuously differs in image quality from its preceding and following frames. A correction amount that is larger than a given threshold value may therefore be added or subtracted in the timekeeping control unit 106 over a period of time in a plurality of installments.

The time request message 207 may include the transmission time of FIG. 7 at which the time request message 207 is transmitted from the radiation imaging apparatus 101, and the time message 208 may include the transmission time at which the time request message 207 is transmitted and a transmission time at which the time message 208 is transmitted. This enables the radiation imaging system to execute processing even when which time request message 207 is associated and paired with which time message 208 becomes unclear due to a message loss.

The first embodiment uses the procedure of FIG. 7 in order to describe a minimum operating principle. However, the time synchronization processing is not limited thereto and, when the present invention is carried out in a mode that tolerates complexity, an existing complex time synchronization protocol may be used. Examples of the known protocol include RFC 4330, SNTP, and IEEE 1588 PTP.

As described above, the system according to the first embodiment is run while executing, in combination, the communication procedure for photographing processing in which the start and stop of photographing are controlled and the communication procedure for synchronization processing in which times measured by a plurality of timekeeping control units are synchronized. The communication procedures are not exclusive and are not always required to cooperate with each other.

That is, the communication procedure for the time synchronization processing may be executed while photographing is conducted and the normality message 202 is periodically transmitted. When photographing takes time, the time difference between the once synchronized timekeeping control units 106 and 122 increases again, and the communication procedure for the time synchronization processing may be executed periodically during photographing. On the other hand, it is not always required to correlate the interval of the normality message 202 and the interval of the time request message 207, and the operation of transmitting the normality message 202 and the operation of transmitting the time request message 207 may be executed at different intervals. However, the intervals of a plurality of messages may be correlated for the purpose of improving the precision of synchronization while avoiding a temporal overlap between the transmission and reception of messages, or other purposes.

The correction amount is statistically calculated as a result of the communication procedure for the time synchronization processing as described above. The result of this statistical processing may affect control on the start and stop of photographing in some cases. When the dispersion of a plurality of correction amounts obtained from a plurality of time request messages 207 is greater than a given threshold value, it is difficult to obtain a truly required correction amount, and it is unlikely that time synchronization is successfully established prior to the correction. Accordingly, when the correction amount has a low degree of certainty, it is regarded that time synchronization is not established, and the radiation imaging system may prohibit photographing from starting or perform control that interrupts photographing.

The irradiation control apparatus 120 or the radiation imaging apparatus 101 thus stops operation related to the irradiation or detection of radiation when a statistical value about a variation (dispersion, standard deviation, or the like) in correction amount of the time information exceeds a given threshold value.

Specifically, control is performed to prevent the radiation imaging apparatus 101 from transmitting the photographing permission message 201 in response to the photographing request message 200. The radiation imaging apparatus 101 may also be controlled so that the radiation imaging apparatus 101 discontinues the transmission of the normality message 202 during photographing and starts transmitting the abnormality message 204. The degree of certainty of synchronization serving as a criterion for the prohibition or interruption of photographing may be variable depending on a parameter for the photographing of a moving image. The given threshold value for the statistical value about the variation (dispersion, standard deviation, or the like) in correction amount of the time information is variable depending on a radiation irradiation condition or a radiation detection condition.

For example, the radiation imaging system may be configured so that photographing is executable even at a low degree of certainty of time synchronization because a period in which radiation is detected can be set long when the frame rate is lower than a given threshold value.

Second Embodiment

In the first embodiment, the timekeeping control unit 122 included in the irradiation control apparatus 120 serves as a reference timekeeping unit (master clock) providing reference by which the radiation imaging system operates. The present invention, however, is not limited thereto. The timekeeping control unit 106 included in the radiation imaging apparatus 101 may serve as a reference timekeeping unit (master clock) providing reference by which the radiation imaging system operates. In this case, the irradiation control apparatus 120 corrects the time information that is referred to by the irradiation control apparatus 120 (the time measured by the timekeeping control unit 122) based on the time information that is referred to by the radiation imaging apparatus 101 (the time measured by the timekeeping control unit 106).

For example, the irradiation control apparatus 120 corrects the time information that is referred to by the irradiation control apparatus 120 based on the time information that is referred to by the radiation imaging apparatus 101, a transmission time at which time request information is transmitted, and a reception time at which time information is received, as in the synchronization processing of the radiation imaging apparatus 101 described above. The time request information in this case is a time request message requesting the radiation imaging apparatus 101 to transmit the time (time information) that is measured by the timekeeping control unit 106. The time information in this case is a time message sent from the radiation imaging apparatus 101 in response to the time request message.

Figure 8:
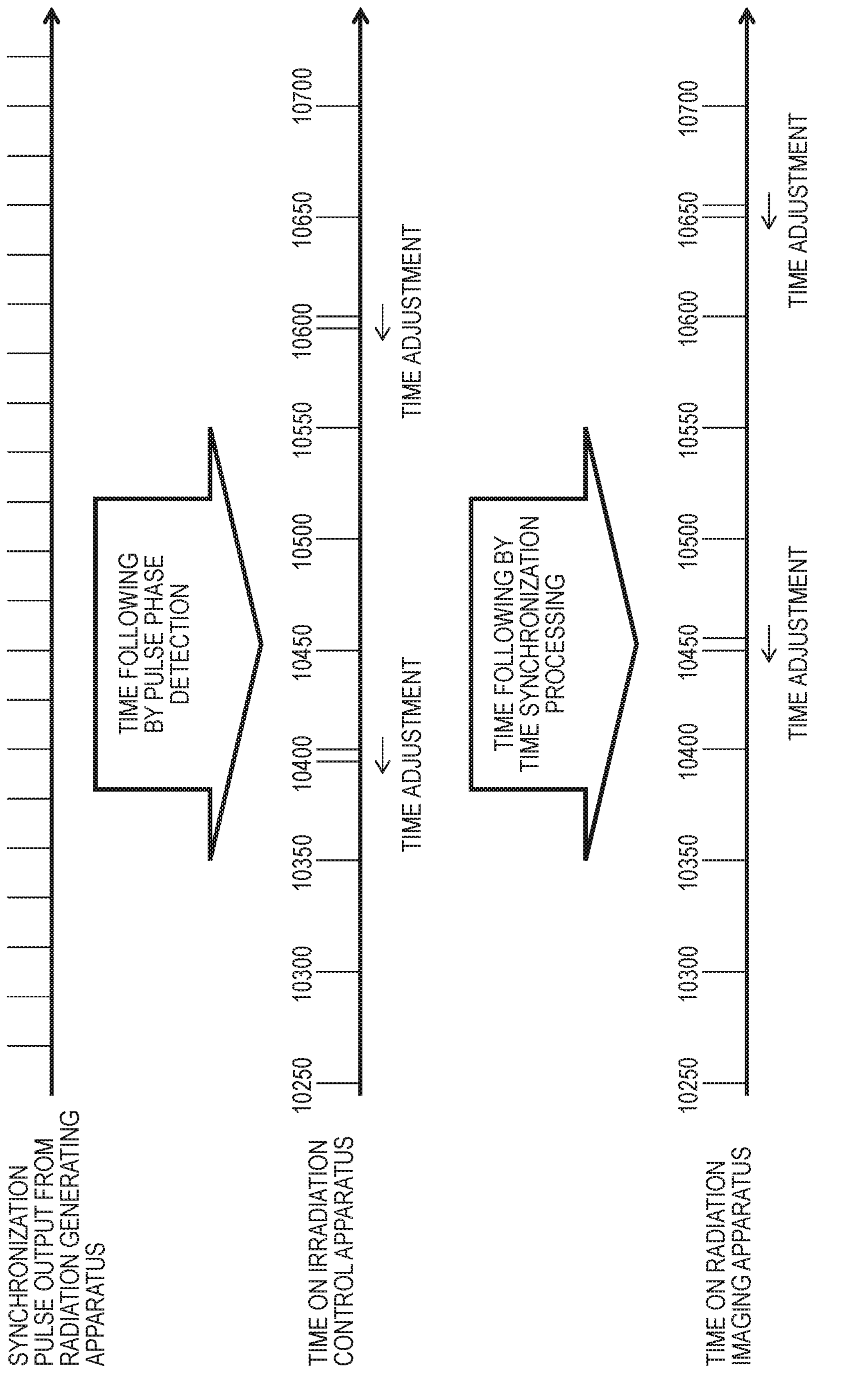
FIG. 8 is a diagram for illustrating an example of time synchronization processing in which a radiation generating apparatus serves as a master clock.

The irradiation control apparatus 120 may also correct the time information that is referred to by the irradiation control apparatus 120 based on a synchronization pulse of the radiation generating apparatus 110. Time synchronization operation in a system configured so that a pulse according to the frame rate of photographing is generated by the radiation generating apparatus 110 to be followed by the timekeeping control unit 122 is illustrated in FIG. 8. The irradiation control apparatus 120 may thus correct the time information that is referred to by the irradiation control apparatus 120 (the time measured by the timekeeping control unit 122) based on time information that is referred to by the radiation generating apparatus 110 (the synchronization pulse).

The radiation generating apparatus 110 periodically generates a synchronization pulse according to the frame rate of photographing, and transmits the synchronization pulse to the irradiation control apparatus 120. The radiation generating apparatus 110 withholds the execution of exposure despite the generation of the synchronization pulse, unless an exposure permission is received from the irradiation control apparatus 120.

The radiation generating apparatus 110 generates the synchronization pulse according to a source oscillator that is included in the radiation generating apparatus 110, and an error between the synchronization pulse and how far ahead or behind the time measured by the timekeeping control unit 122 of the irradiation control apparatus 120 is cannot be eliminated completely. When synchronization is not established, an error between the synchronization pulse of the radiation generating apparatus 110 and the time on the irradiation control apparatus 120 increases, resulting in a situation in which the synchronization pulse is not generated at a pulse generation time calculated based on the time that is measured by the timekeeping control unit 122.

To deal with this, the irradiation control apparatus 120 compares a synchronization pulse generation time provided to the irradiation control apparatus 120 with the time measured by the timekeeping control unit 122 and, when a difference between the two is detected, corrects the timekeeping control unit 122 so that the timekeeping control unit 122 follows the synchronization pulse. The radiation generating apparatus 110 and the irradiation control apparatus 120 are connected electrically and directly to each other without an intervening communication network. An estimated value of the correction amount is therefore small in fluctuation that is caused by the communication network. Accordingly, statistical processing for calculating a true correction value is not required, and correction of the time difference immediately after the detection of the difference is sufficient. This enables the timekeeping control unit 122 to follow the synchronization pulse with precision.

The operation of synchronizing the time that is measured by the timekeeping control unit 122 and the time that is measured by the timekeeping control unit 106 is executed in the same manner as in the first embodiment. When the timekeeping control unit 122 follows the synchronization pulse, the timekeeping control unit 106 follows with a small delay. The difference between the synchronization pulse and the time measured by the timekeeping control unit 106 is accordingly expected to be larger than in the first embodiment. However, the larger difference does not affect much on the whole in practice since the operation of the timekeeping control unit 122 to follow the synchronization pulse is precise as described above.

Figure 9:
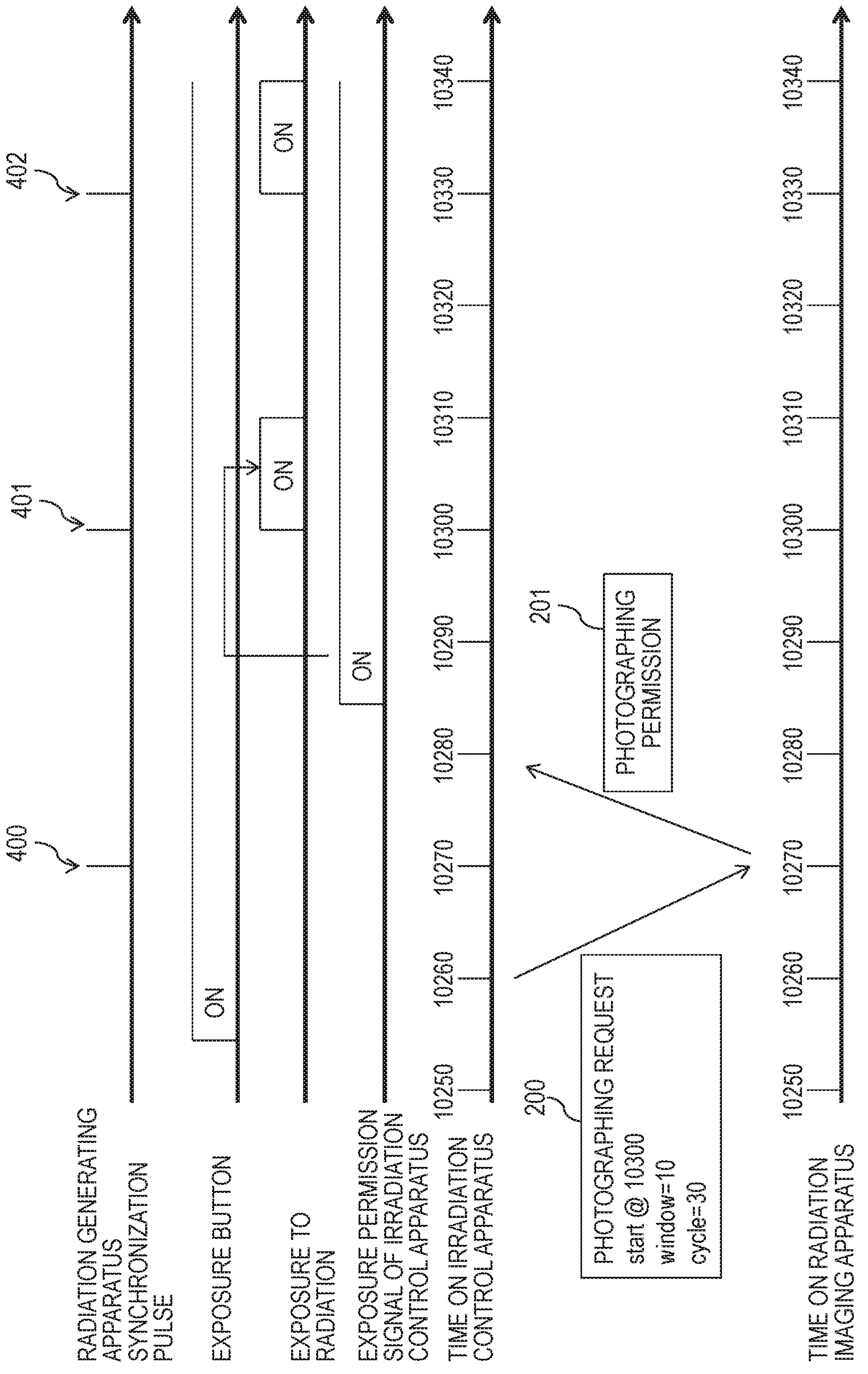
FIG. 9 is a diagram for illustrating an example of a communication procedure for starting photographing in which the radiation generating apparatus serves as a master clock.

Operation executed at the start of photographing in the second embodiment is illustrated in FIG. 9. When detecting the press of the exposure button, the irradiation control apparatus 120 predicts times at which synchronization pulses 400, 401, and 402 are generated subsequently to the press of the exposure button, in terms of time measured by the timekeeping control unit 122. The irradiation control apparatus 120 takes into consideration the time required for the photographing preparation operation of the radiation imaging apparatus 101 and the like, in determining a synchronization pulse time that corresponds to the scheduled exposure start time and that is predicted to allow the photographing operation to be ready, out of the synchronization pulses 400, 401, and 402. In FIG. 9, the synchronization pulse 401 is employed as the scheduled exposure start time. Subsequent exchanges of messages are executed by the same procedure that is used in the first embodiment, and a description on the procedure is therefore omitted.

The irradiation control apparatus 120 receives the photographing permission message 201 and notifies the radiation generating apparatus 110 that photographing has been permitted. The radiation generating apparatus 110 receives the notification and generates radiation in time with the generation of the synchronization pulse by the radiation generating apparatus 110.

Third Embodiment

The present invention also includes a case in which a timekeeping unit other than the timekeeping control units 106 and 122 is present in the communication network and is used as a master clock. The radiation imaging apparatus 101 corrects the time information that is referred to by the radiation imaging apparatus 101 (the time measured by the timekeeping control unit 106) based on the master clock serving as a reference (reference time information). The irradiation control apparatus 120 similarly corrects the time information that is referred to by the irradiation control apparatus 120 (the time measured by the timekeeping control unit 122) based on the master clock serving as a reference (the reference time information).

Figure 10:
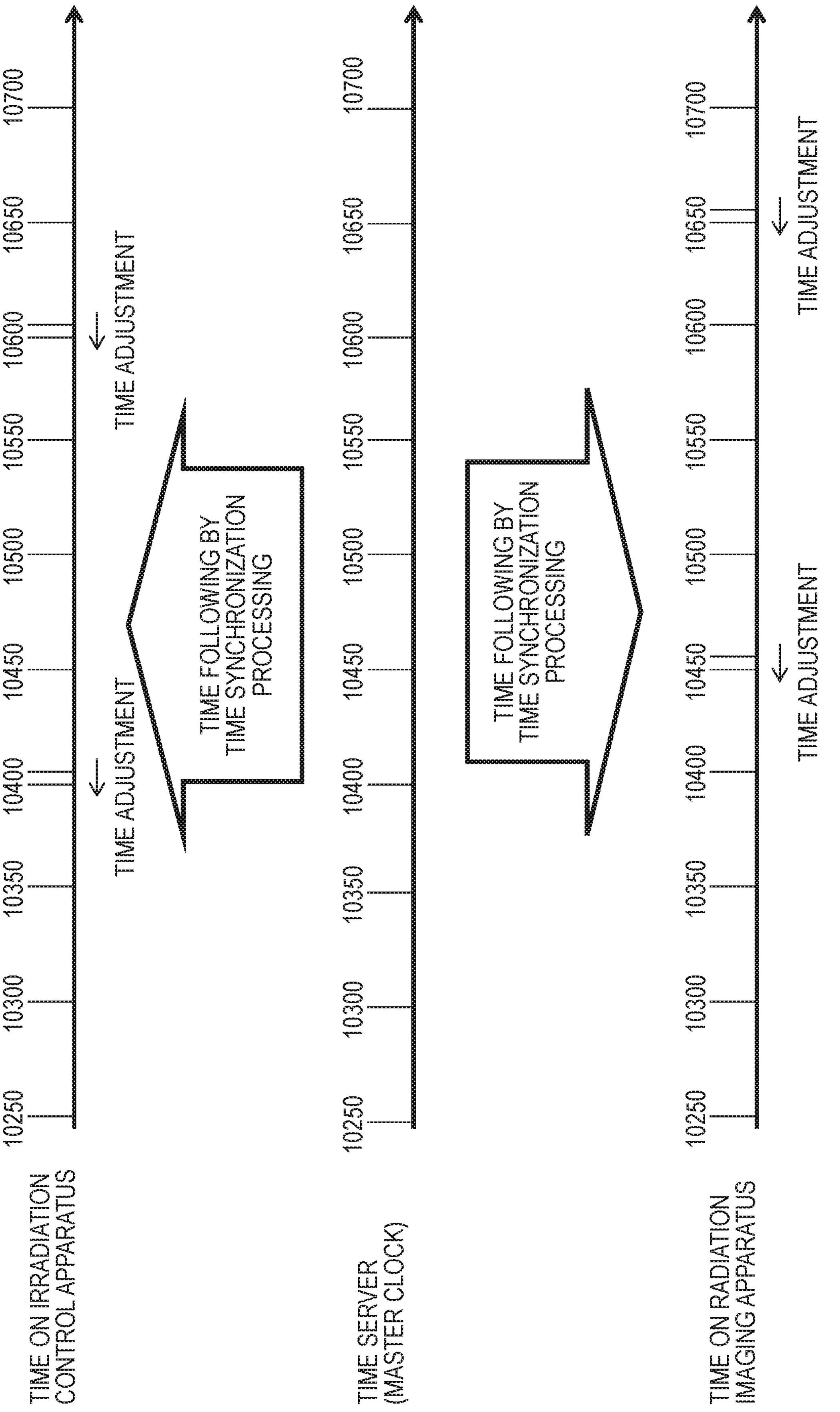
FIG. 10 is a diagram for illustrating an example of time synchronization processing in which an independent master clock node is used.

As illustrated in FIG. 10, a radiation imaging system according to the third embodiment includes a time server, which serves as the master clock (reference time information), in the communication network in addition to the system configuration of FIG. 1. The time server executes processing similar to the processing that is executed by the timekeeping control unit 122 of the first embodiment in FIG.

7. The timekeeping control unit 122 of the third embodiment operates as a time client unlike the timekeeping control unit 122 of the first embodiment.

The timekeeping control unit 106 and the timekeeping control unit 122 both hold communication to and from the time server of FIG. 10, and correct the time measured by the timekeeping control unit 106 and the time measured by the timekeeping control unit 122 to follow the time server.

In the first embodiment, the timekeeping control unit 106 is a time client and accordingly conducts statistical estimation of the correction amount. In the third embodiment, the timekeeping control unit 122 is a time client as well, and accordingly executes the same operation as the operation of the timekeeping control unit 106. This lowers the degree of certainty of synchronization when the timekeeping control unit 122 of the irradiation control apparatus 120 executes processing of synchronizing with the master clock, thereby creating a risk of synchronization error for the timekeeping control unit 122.

In the example described in the first embodiment, control that prevents the radiation imaging apparatus 101 from permitting photographing is performed when the correction amount has a low degree of certainty. In the third embodiment, control that prevents the irradiation control apparatus 120 from permitting radiation irradiation may be performed when the correction amount has a low degree of certainty.

Specifically, the irradiation control apparatus 120 ignores a press of the exposure button when the degree of certainty is low, and executes the operation of, for example, withholding the transmission of the photographing request message 200 to the radiation imaging apparatus 101.

Fourth Embodiment

In the first embodiment, it is assumed that, as illustrated in FIG. 7, the time request message and the time message in response are substantially equal to each other in propagation time in the communication procedure for time synchronization. However, a message transmitted over a communication network and a message received over the communication network may not be equal to each other in propagation time in some cases. The asymmetry in propagation time is prominent particularly in communication between an access point (AP) of a wireless LAN and wireless stations.

Figure 11:
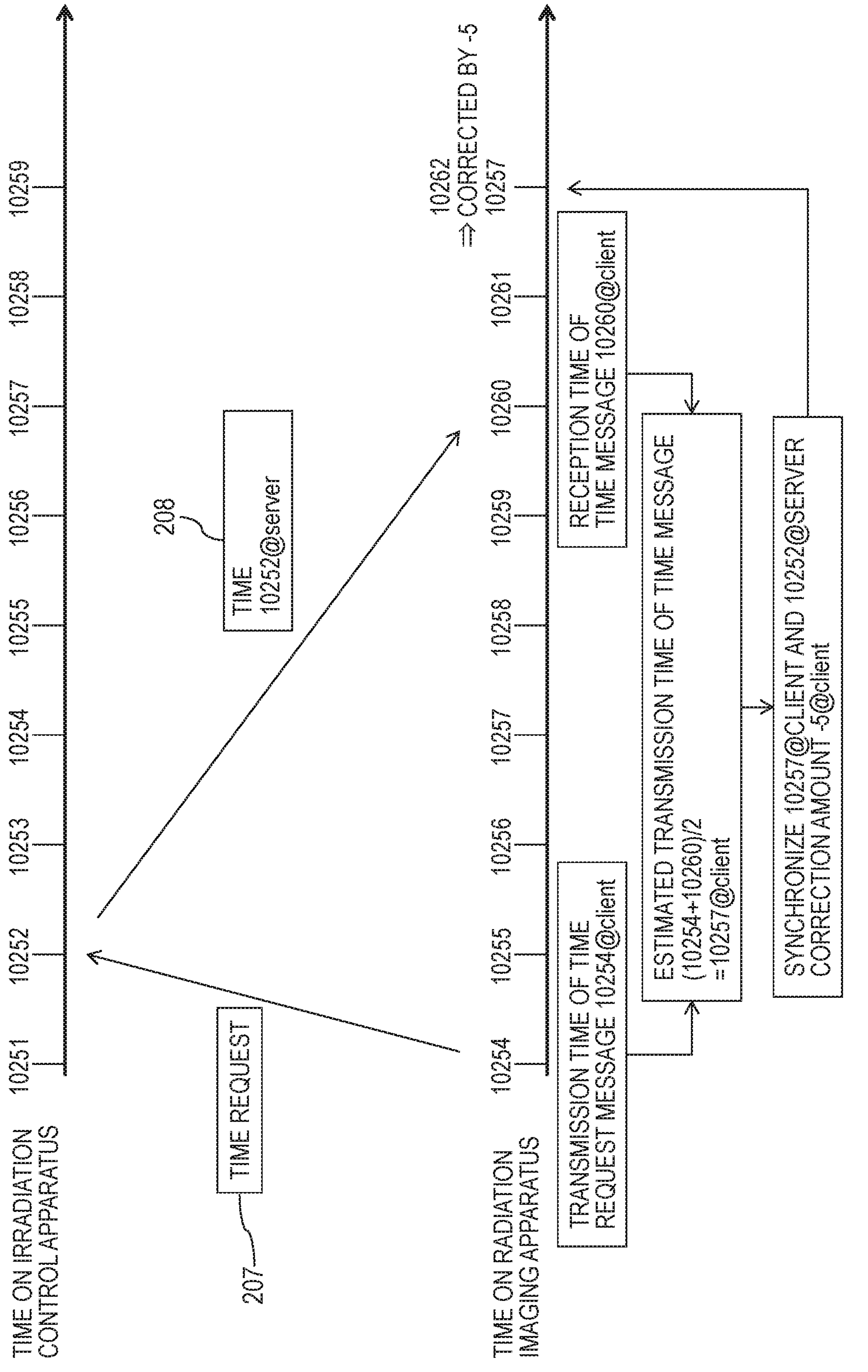
FIG. 11 is a diagram for illustrating an example of time synchronization processing that is executed when there is a difference in propagation time between message transmission and message reception.

How a communication procedure for time synchronization is executed in this type of communication network is illustrated in FIG. 11. In FIG. 11, the time measured by the timekeeping control unit 122 after synchronization processing is executed is 10259, whereas the time indicated by the timekeeping control unit 106 is 10257, which means that a gap is still caused by the asymmetry in propagation time after correction. When the asymmetry is not transitory but consistent, repeated execution of the synchronization processing does not solve the time difference caused by the asymmetry.

To deal with this, the wired communication unit 104 and the wireless communication unit 103 may be connected simultaneously to the communication network when the radiation imaging system 100 is activated, so that a time synchronization procedure is executed for the timekeeping control unit 106 by both of the communication units. After the time synchronization is executed by temporarily using the wired communication unit 104 and the wireless communication unit 103, a time at which synchronization has been executed with the wired communication unit 104 is set as true, and a time at which synchronization has been executed with the wireless communication unit 103 is assumed to include a steady correction gap. Then, a difference between the former time and the latter time is a correction gap of the synchronization processing in the wireless communication unit.

As described above, a consistent correction gap can be solved by modifying the correction amount with the calculated correction gap, despite continued use of the wireless communication unit in the subsequent synchronization processing.

The radiation imaging apparatus 101 is thus capable of holding communication to and from the irradiation control apparatus 120 through a first communication unit (wired communication) and a second communication unit (wireless communication), with which time information is propagated.

The radiation imaging apparatus 101 executes first correction processing in which time information that is referred to by the radiation imaging apparatus 101 (the time measured by the timekeeping control unit 106) is corrected based on time information that is received from the irradiation control apparatus 120 through the first communication unit (the time measured by the timekeeping control unit 122). Further, the radiation imaging apparatus 101 executes second correction processing in which time information that is referred to by the radiation imaging apparatus 101 (the time measured by the timekeeping control unit 106) is corrected based on time information that is received from the irradiation control apparatus 120 through the second communication unit (the time measured by the timekeeping control unit 122).

The radiation imaging apparatus 101 modifies a correction amount that is obtained in the second correction processing with a correction amount that is obtained in the first correction processing. In this case, an error between the pieces of time information in the first correction processing is smaller than an error between the pieces of time information in the second correction processing, and the correction amount obtained in the second correction processing is therefore modified with the time corrected by the first correction processing as a true time.

In the fourth embodiment, the synchronization time at which synchronization is executed with the wired communication unit 104 is used as a true synchronization time. However, the present invention is not limited thereto. The true synchronization time may be set with the use of, for example, a direct synchronization unit for establishing synchronization without an intervening communication network.

Fifth Embodiment

In the first embodiment, it is mentioned that the communication procedure for synchronization processing may be continued during photographing in order to prevent the time difference between the radiation imaging apparatus 101 and the irradiation control apparatus 120 from increasing. The time difference can also be prevented from increasing rapidly despite interruption to the communication procedure for synchronization processing by giving a source oscillator of the timekeeping control unit 106 of the radiation imaging apparatus 101 and a source oscillator of the timekeeping control unit 122 of the irradiation control apparatus 120 a level of precision at which cycles of the oscillators are very close to each other without correction.

This can be used to stop the communication procedure for synchronization processing during the execution of photographing or at other times. However, a prolonged suspension period in which the synchronization processing is stopped inevitably increases the time difference. Accordingly, a maximum time difference caused by the suspension period may be estimated based on the length of the suspension period so that the synchronization processing is executed again when the estimated maximum time difference exceeds a given threshold value. Specifically, the operator is alerted and requested to execute the synchronization processing again when a certain time elapses since the synchronization processing is executed last.

The method of time synchronization is not limited to the communication procedure described in the first embodiment, and may be synchronization method for establishing synchronization without an intervening communication network. For example, the irradiation control apparatus 120 and the radiation imaging apparatus 101 are synchronized by direct electric connection, the direct electric connection is then disconnected to execute photographing operation, and, when a certain time elapses since the disconnection, the photographing operation is automatically interrupted and the operator is requested to execute the synchronization processing again.

According to the first embodiment to the fifth embodiment described above, photographing can be conducted while the radiation generating apparatus and the radiation imaging apparatus are synchronized, and unnecessary exposure can be avoided by stopping radiation irradiation when a situation in which synchronization is not possible is presumed. In addition, the precision of photographing synchronization can be improved by executing the time synchronization processing.

The embodiments of the present invention have been described above, but the present invention is not limited thereto, and changes and modifications can be made thereto within the scope of the appended claims.

For instance, the irradiation control apparatus 120 and the radiation imaging apparatus 101 each include an internal clock (the timekeeping control units 122 and 106), and the radiation imaging apparatus 101 executes photographing operation based on the time of its own internal clock. The irradiation control apparatus 120 controls pulse-like radiation irradiation based on the time of its own internal clock and a time difference between the irradiation control apparatus 120 and the radiation imaging apparatus 101.

The radiation imaging system 100 includes at least the irradiation control apparatus 120, which controls the timing of pulse-like radiation irradiation, and one or more radiation imaging apparatus 101, and the irradiation control apparatus 120 and the one or more radiation imaging apparatus 101 are connected to one another by a communication network line.

The irradiation control apparatus 120 transmits a message containing a time at which pulse irradiation of radiation is to be executed over the communication network line to each radiation imaging apparatus 101 in the radiation imaging system. Each radiation imaging apparatus 101 receives the message, and transmits a confirmation response to the irradiation control apparatus 120. When the confirmation response is received from every radiation imaging apparatus 101 to which the message has been transmitted, the irradiation control apparatus 120 continues pulse-like radiation irradiation at a specific frame interval. When the confirmation response is not received within a given number of timing pulses, the irradiation control apparatus 120 stops irradiation.

The irradiation control apparatus 120 or the radiation imaging apparatus 101 calculates a change with time in correction amount based on the correction amount of the time information, and estimates the correction amount based on the change with time. When the estimated correction amount exceeds a given threshold value, the irradiation control apparatus 120 executes at least one of the correction of the time information that is referred to by the irradiation control apparatus 120 and the stopping of operation related to radiation irradiation. When the estimated correction amount exceeds the given threshold value, the radiation imaging apparatus 101 executes at least one of the correction of the time information that is referred to by the radiation imaging apparatus 101 and the stopping of operation related to radiation detection.

For example, the correction amount is estimated from a change with time by correcting the time information a plurality of times as described above, calculating the amounts of change per unit time of the amounts of the corrections, and multiplying an average of the amounts of change by the elapsed time.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A radiation imaging system comprising:

an irradiation control apparatus configured to control an irradiation unit arranged to irradiate with radiation so that irradiation with radiation is executed at an irradiation time at which irradiation of the radiation is to be started by the irradiation unit;

a radiation imaging apparatus including:

a detection unit arranged to detect the radiation; and a control unit configured to control the detection unit so that the detection unit is ready to detect the radiation at the irradiation time, wherein, if the detection unit is expected to be ready to detect the radiation at the irradiation time, the control unit transmits photographing permission information, which indicates that the detection unit is ready to detect the radiation at the irradiation time, to the irradiation control apparatus and performs photographing preparation operation.

2. The radiation imaging system according to claim 1, wherein, if the detection unit is not expected to be ready to detect the radiation at the irradiation time, the control unit transmits photographing prohibition information to the irradiation control apparatus.

3. The radiation imaging system according to claim 2, wherein the irradiation control apparatus is configured to:

perform control so that the irradiation unit irradiates with the radiation if the photographing permission information is received by a point in time that precedes the irradiation time by a given amount; and perform control that prevents the irradiation unit from irradiating with the radiation if the photographing permission information is not received by the point in time that precedes the irradiation time by the given amount.

4. The radiation imaging system according to claim 1, wherein, if the detection unit is allowed to detect radiation, the control unit transmits normality information, which indicates that the detection unit is operating normally, to the irradiation control apparatus, and wherein the irradiation control apparatus performs control so that the irradiation unit irradiates with the radiation, based on the normality information.

5. The radiation imaging system according to claim 4, wherein the irradiation control apparatus performs control so that the irradiation unit irradiates with the radiation, based on at least one of reception/non-reception of the normality information, a frequency of the reception, an interval of the reception, a time of the reception, and the number of received pieces of normality information.

6. The radiation imaging system according to claim 4, wherein, if the detection unit is unavailable to detect radiation, the control unit transmits abnormality information as the photographing prohibition information, which indicates that the detection unit is not operating normally, to the irradiation control apparatus, and wherein the irradiation control apparatus performs control so that the irradiation unit does not irradiate with the radiation, based on the abnormality information.

7. The radiation imaging system according to claim 6, wherein, if the irradiation control apparatus receives the abnormality information, the irradiation control apparatus determines that there is abnormality in the detection unit, and performs control that prevents the irradiation unit from irradiating with the radiation.

8. The radiation imaging system according to claim 1, wherein, if the irradiation unit stops irradiating with the radiation, the irradiation control apparatus transmits stop request information requesting the detection unit to stop operating to the control unit.

9. The radiation imaging system according to claim 8, wherein, if the control unit receives the stop request information, the control unit transmits response information indicating that the stop request information has been received to the irradiation control apparatus, and wherein, if the irradiation control apparatus receives the response information, the irradiation control apparatus stops transmitting the stop request information.

10. The radiation imaging system according to claim 1, wherein the control unit corrects time information that is referred to by the control unit based on time information that is referred to by the irradiation control apparatus, or on reference time information which serves as a reference.

11. The radiation imaging system according to claim 10, wherein, if a statistical value about a variation in correction amount of the time information exceeds a given threshold value, one of the irradiation control apparatus and the control unit stops operation related to one of irradiation and detection of the radiation.

12. The radiation imaging system according to claim 11, wherein the given threshold value is variable depending on an irradiation condition of the radiation or a detection condition of the radiation.

13. The radiation imaging system according to claim 10, wherein one of the irradiation control apparatus and the control unit is configured to:

calculate, based on a correction amount of the time information, a change with time of the correction amount;

estimate the correction amount based on the change with time; and execute, if the estimated correction amount exceeds a given threshold value, at least one of correction of the time information that is referred to by the irradiation control apparatus, correction of the time information that is referred to by the control unit, stopping of operation that is related to irradiation of the radiation, and stopping of operation that is related to detection of the radiation.

14. The radiation imaging system according to claim 10, wherein the control unit is configured to:

hold communication to and from the irradiation control apparatus through a first communication unit and a second communication unit configured to propagate the time information;

execute first correction processing in which the time information that is referred to by the control unit is corrected based on the time information that is received from the irradiation control apparatus via the first communication unit;

execute second correction processing in which the time information that is referred to by the control unit is corrected based on the time information that is received from the irradiation control apparatus via the second communication unit; and modify a correction amount that is obtained in the second correction processing, based on a correction amount that is obtained in the first correction processing.

15. The radiation imaging system according to claim 14, wherein an error between pieces of the time information in the first correction processing is smaller than an error between pieces of the time information in the second correction processing.

16. The radiation imaging system according to claim 1, wherein the control unit corrects time information that is referred to by the control unit based on time information that is referred to by the irradiation control apparatus, a transmission time at which time request information requesting the irradiation control apparatus to transmit the time information is transmitted, and a reception time at which the time information is received from the irradiation control apparatus in response to the time request information.

17. The radiation imaging system according to claim 1, wherein the irradiation control apparatus corrects time information that is referred to by the irradiation control apparatus based on time information that is referred to by the control unit, time information that is referred to by the irradiation unit, and reference time information which serves as a reference.

18. The radiation imaging system according to claim 1, wherein the irradiation control apparatus is configured to:

receive, if the detection unit is allowed to detect the radiation, normality information indicating that the detection unit is operating normally, from the control unit;

receive, if the detection unit is unavailable to detect the radiation, abnormality information indicating that the detection unit is not operating normally from the control unit;

determine the detection unit as one of normal and abnormal based on one of the normality information and the abnormality information; and perform control that causes the irradiation unit to irradiate with the radiation if the detection unit is normal, and perform control that prevents the irradiation unit from irradiating with the radiation if the detection unit is abnormal.

19. The radiation imaging system according to claim 1, wherein the radiation imaging apparatus is capable of photographing a moving image.

20. A radiation imaging method comprising the steps of:

setting an irradiation time at which irradiation of radiation is to be started;

controlling, by an irradiation control apparatus, an irradiation unit of the radiation so that irradiation of the radiation is executed at the irradiation time;

controlling a detection unit of the radiation so that the detection unit is ready to detect the radiation at the irradiation time;

transmitting photographing permission information, which indicates that the detection unit is expected to be ready to detect the radiation at the irradiation time, to the irradiation control apparatus, if the detection unit is expected to be ready to detect the radiation at the irradiation time; and performing photographing preparation operation in a time period between a time at which the photographing permission information is transmitted and the irradiation time.

21. A non-transitory computer-readable medium having stored thereon a program for causing, when being executed by a processor, the processor to perform respective steps of the radiation imaging method of claim 20.

22. A radiation imaging apparatus comprising:

a detection unit arranged to detect radiation from an irradiation unit arranged to irradiate with the radiation;

a reception unit configured to receive, from an external apparatus, irradiation information about an irradiation time at which irradiation of the radiation is to be started;

a control unit configured to control the detection unit so that the detection unit is ready to detect the radiation at the irradiation time, based on the irradiation information; and a transmission unit configured to transmit photographing permission information, which indicates that the detection unit is ready to detect the radiation at the irradiation time, to the external apparatus if the detection unit is expected to be ready to detect the radiation at the irradiation time, wherein the control unit performs photographing preparation operation in a time period between a time at which the photographing permission information is transmitted and the irradiation time.

23. The radiation imaging apparatus according to claim 22, wherein the control unit corrects time information that is referred to by the control unit based on time information that is referred to by the external apparatus, a transmission time at which time request information requesting the external apparatus to transmit the time information is transmitted, and a reception time at which the time information is received from the external apparatus in response to the time request information.

24. The radiation imaging apparatus according to claim 23, wherein, if a statistical value about a variation in correction amount of the time information exceeds a given threshold value, the control unit stops detection operation of the radiation by the detection unit.

25. The radiation imaging apparatus according to claim 24, wherein the given threshold value is variable depending on a detection condition of the radiation.

26. The radiation imaging apparatus according to claim 24, wherein the control unit is configured to:

calculate, based on a correction amount of the time information, a change with time of the correction amount;

estimate the correction amount based on the change with time; and execute, if the estimated correction amount exceeds a given threshold value, at least one of correction of the time information that is referred to by the control unit, and stopping of detection operation of the radiation by the detection unit.

27. The radiation imaging apparatus according to claim 23, wherein the control unit is configured to:

hold communication to and from the external apparatus through a first communication unit and a second communication unit configured to propagate the time information;

execute first correction processing in which the time information that is referred to by the control unit is corrected based on the time information that is received from the external apparatus via the first communication unit;

execute second correction processing in which the time information that is referred to by the control unit is corrected based on the time information that is received from the external apparatus via the second communication unit; and modify a correction amount that is obtained in the second correction processing, based on a correction amount that is obtained in the first correction processing.

28. The radiation imaging apparatus according to claim 27, wherein an error between pieces of the time information in the first correction processing is smaller than an error between pieces of the time information in the second correction processing.

* * * * *